(12) United States Patent
Miyazaki

(10) Patent No.: US 9,168,337 B2
(45) Date of Patent: Oct. 27, 2015

(54) FLUID INJECTING APPARATUS

(71) Applicant: SEIKO EPSON CORPORATION, Tokyo (JP)

(72) Inventor: Hajime Miyazaki, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 1 day.

(21) Appl. No.: 14/057,423

(22) Filed: Oct. 18, 2013

(65) Prior Publication Data

US 2014/0114251 A1    Apr. 24, 2014

(30) Foreign Application Priority Data

Oct. 22, 2012  (JP) .................................. 2012-232578

(51) Int. Cl.
*A61M 5/14* (2006.01)
*A61M 5/142* (2006.01)
*A61M 5/168* (2006.01)

(52) U.S. Cl.
CPC ....... *A61M 5/14228* (2013.01); *A61M 5/14248* (2013.01); *A61M 5/16804* (2013.01); *A61M 5/16813* (2013.01); *A61M 5/1413* (2013.01); *A61M 5/14232* (2013.01); *A61M 2005/1416* (2013.01)

(58) Field of Classification Search
CPC .......... A61M 31/002; A61M 5/14276; A61M 5/14244; A61M 5/14566; A61M 5/142; A61M 2005/1404; A61M 2005/1406; A61M 5/1413; A61M 2005/1416; A61M 5/14248; A61K 9/0009
USPC .................. 604/890.1, 151, 131, 232–234
See application file for complete search history.

(56) References Cited

U.S. PATENT DOCUMENTS

| | | | |
|---|---|---|---|
| 5,938,414 A * | 8/1999 | Kayahara et al. ............. | 417/476 |
| 6,740,059 B2 * | 5/2004 | Flaherty ......................... | 604/67 |
| 2009/0076453 A1 * | 3/2009 | Mejlhede et al. ............. | 604/151 |
| 2010/0047099 A1 | 2/2010 | Miyazaki et al. | |
| 2010/0256466 A1 * | 10/2010 | Shekalim et al. ............. | 600/317 |
| 2011/0186143 A1 * | 8/2011 | Miyazaki et al. .............. | 137/67 |
| 2012/0078170 A1 * | 3/2012 | Smith et al. .................... | 604/67 |

FOREIGN PATENT DOCUMENTS

| | | |
|---|---|---|
| JP | A-2005-351131 | 12/2005 |
| JP | A-2010-048121 | 3/2010 |

* cited by examiner

*Primary Examiner* — Bhisma Mehta
*Assistant Examiner* — William Frehe
(74) *Attorney, Agent, or Firm* — Oliff PLC

(57) ABSTRACT

A fluid injecting apparatus includes: a cartridge portion which has a tube that transports a fluid, a plurality of fingers that press the tube, and a blocking member that blocks the tube; and a main body portion which has a cam that presses the plurality of fingers. When the cartridge portion is detached from the main body portion, the blocking member blocks the tube. When the cartridge portion is mounted to the main body portion, the cam presses at least one of the fingers such that the tube is blocked at the position of the pressed finger and the blocking of the tube by the blocking member is released.

11 Claims, 11 Drawing Sheets

FLUID INJECTING APPARATUS

BACKGROUND

1. Technical Field

The present invention relates to a fluid injecting apparatus.

2. Related Art

An insulin pump which injects insulin into a living body is used in practice. A fluid injecting apparatus such as the insulin pump is fixed to a living body such as a human body and regularly injects a fluid to the living body such as a human body according to a program set in advance.

In JP-A-2010-48121, a micropump which is provided with a transport mechanism including a cam, a finger, and a tube and a reservoir is illustrated (FIG. 5).

In a new fluid injecting apparatus illustrated in FIGS. 6 and 7, when a cartridge portion is detached from a main body portion, fingers are freely movable, and thus a fluid in a tube freely flows. Therefore, it is preferable that the fluid in the tube be not allowed to freely flow when the cartridge portion is detached from the main body portion.

SUMMARY

An advantage of some aspects of the invention is that a fluid in a tube is not allowed to freely flow when a cartridge portion is detached from a main body portion.

An aspect of the invention is directed to a fluid injecting apparatus including: a cartridge portion which has a tube that supplies a fluid, a plurality of fingers that sequentially press the tube, and a blocking member that blocks the tube; and a main body portion which has a cam that sequentially presses the plurality of fingers. When the cartridge portion is detached from the main body portion, the blocking member blocks the tube. When the cartridge portion is mounted to the main body portion, the cam presses at least one of the fingers such that the tube is blocked at the position of the pressed finger, the blocking of the tube by the blocking member is released, and thus the tube is open at the position of the blocking member.

Other features of the invention are clarified by the specification and the attached drawings.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
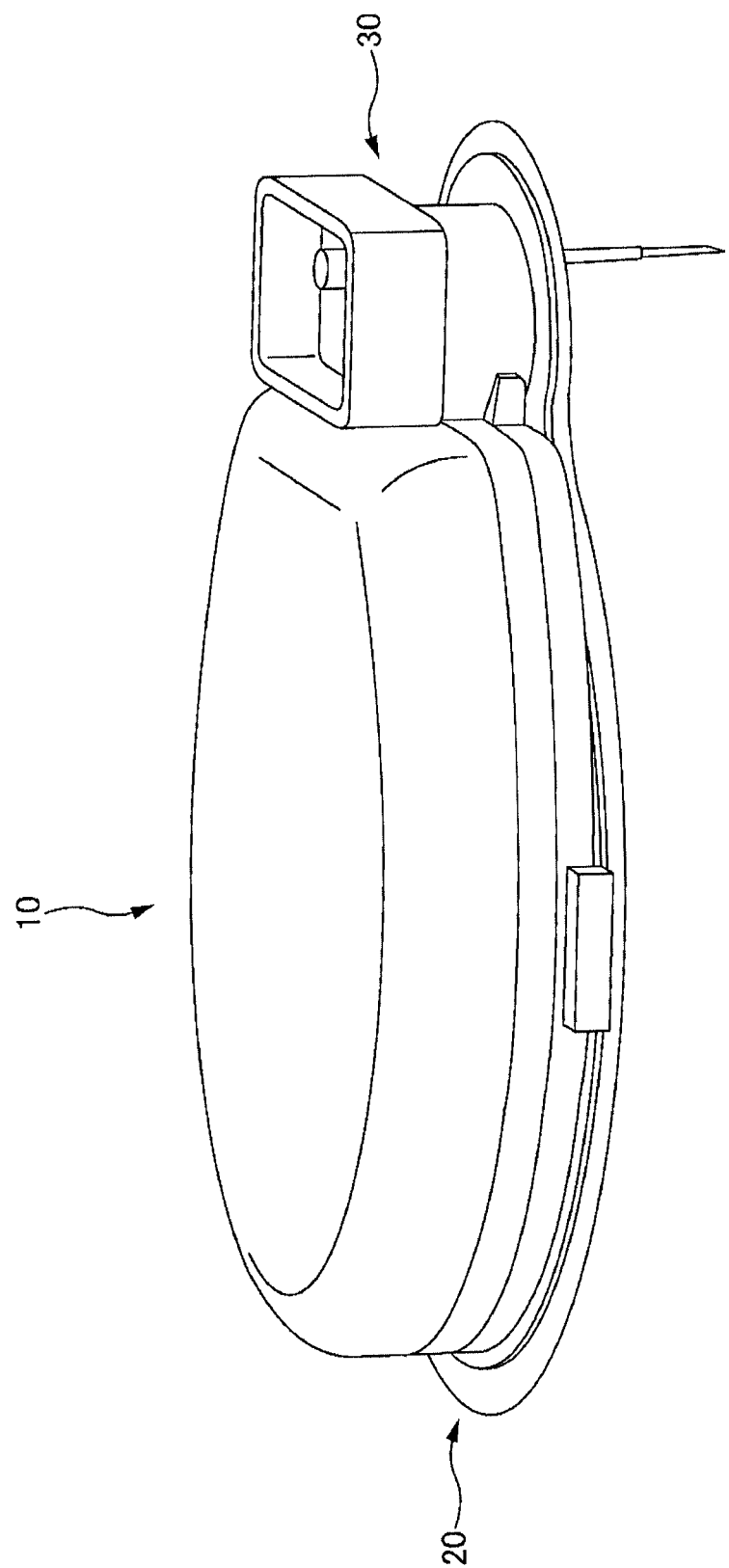
FIG. 1 is a perspective view of the entirety of a micropump.

The following is clarified by the description of the specification and the attached drawings.

A fluid injecting apparatus includes: a cartridge portion which has a tube that supplies a fluid, a plurality of fingers that sequentially press the tube, and a blocking member that blocks the tube; and a main body portion which has a cam that sequentially presses the plurality of fingers. When the cartridge portion is detached from the main body portion, the blocking member blocks the tube. When the cartridge portion is mounted to the main body portion, the cam presses at least one of the fingers such that the tube is blocked at the position of the pressed finger, the blocking of the tube by the blocking member is released, and thus the tube is open at the position of the blocking member.

Accordingly, when the cartridge portion is mounted to the main body portion, the fingers block the tube. On the other hand, in a situation in which the cartridge portion is detached from the main body portion, the cam cannot press the fingers and thus the tube is not blocked, the blocking member can block the tube. Therefore, the fluid in the tube is not allowed to freely flow.

In the fluid injecting apparatus, it is preferable that when the cartridge portion and the main body portion are assembled in one body, a cam surface of the cam portion be disposed at a position that opposes a finger end of the finger.

Accordingly, when the cartridge portion is mounted to the main body portion, one end of the finger comes in contact with the cam surface and the other end of the finger comes in contact with the tube. Therefore, the tube can be blocked by the finger.

In addition, it is preferable that the main body portion include an engagement member, the cartridge portion include an impelling member that impels the blocking member in a direction toward the tube, when the cartridge portion is mounted to the main body portion, the engagement member be engaged so that the blocking member is in a state of not blocking the tube, and when the cartridge portion is detached from the main body portion, the engagement be released and the blocking member block the tube by the impelling force of the impelling member.

Accordingly, when the cartridge portion is detached from the main body portion, the tube can be blocked by the impelling force of the impelling member.

In addition, it is preferable that a guide member which guides a movement of the blocking member in a direction toward the tube be included.

Accordingly, the blocking member can be moved in the direction toward the tube along the guide member.

In addition, it is preferable that the tube contain an elastic material that is deformable.

Accordingly, as the tube is sequentially blocked by the fingers, the fluid is allowed to flow in a predetermined direction.

In addition, it is preferable that the blocking member be provided on a downstream side of the fingers in a transport direction of the fluid in the tube.

Accordingly, there is concern that the tube may be pressed by the fingers that freely move when the cartridge portion is detached from the main body portion. However, since the tube is blocked by the blocking member provided on the downstream side thereof, the fluid can be prevented from freely flowing toward the downstream side.

In addition, it is preferable that a needle member which is inserted into a living body be included on the downstream side of the blocking member in the flowing direction of the fluid in the tube, and a storage portion which stores the fluid be included on an upstream side of the fingers.

Accordingly, the fluid stored in the storage portion can be sent to the living body.

In addition, it is preferable that a pressure sensor that detects a pressure of the tube be included in the main body portion, and the detachment of the cartridge portion from the main body portion be detected on the basis of the detection value of the pressure sensor.

Accordingly, the detachment of the cartridge portion from the main body portion can be detected by using the pressure sensor that is used to detect the pressure of the tube.

Embodiment

Figure 2:
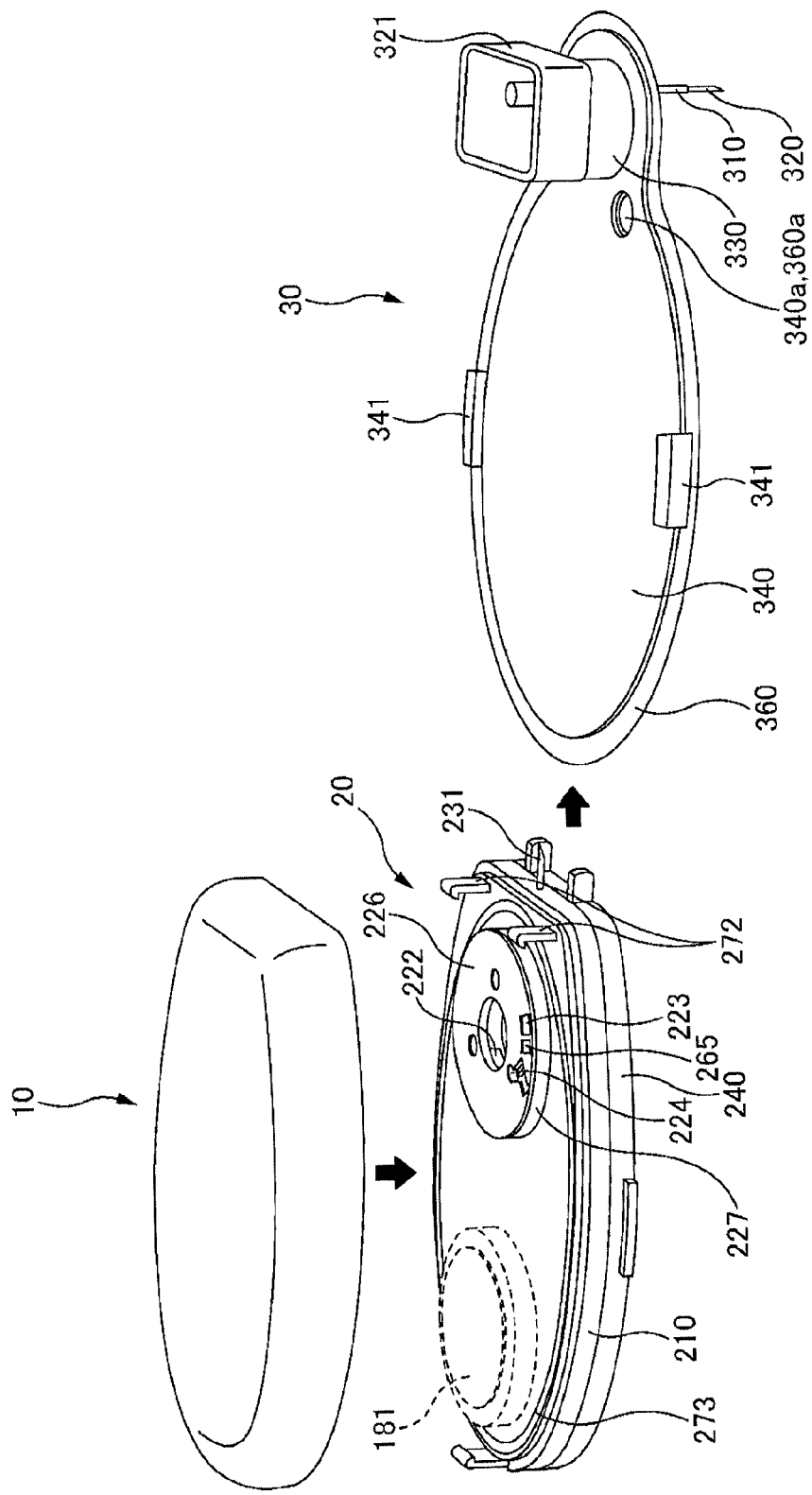
FIG. 2 is an exploded view of the micropump.

FIG. 1 is a perspective view of the entirety of a micropump 1. FIG. 2 is an exploded view of the micropump 1. The micropump 1 includes a main body 10, a cartridge 20, and an injection set 30. The three components can be disassembled as illustrated in FIG. 2 and can be assembled in one body in use as illustrated in FIG. 1. The micropump 1 in this embodiment sticks to a living body and is appropriately used for a regular injection of insulin.

Figure 3:
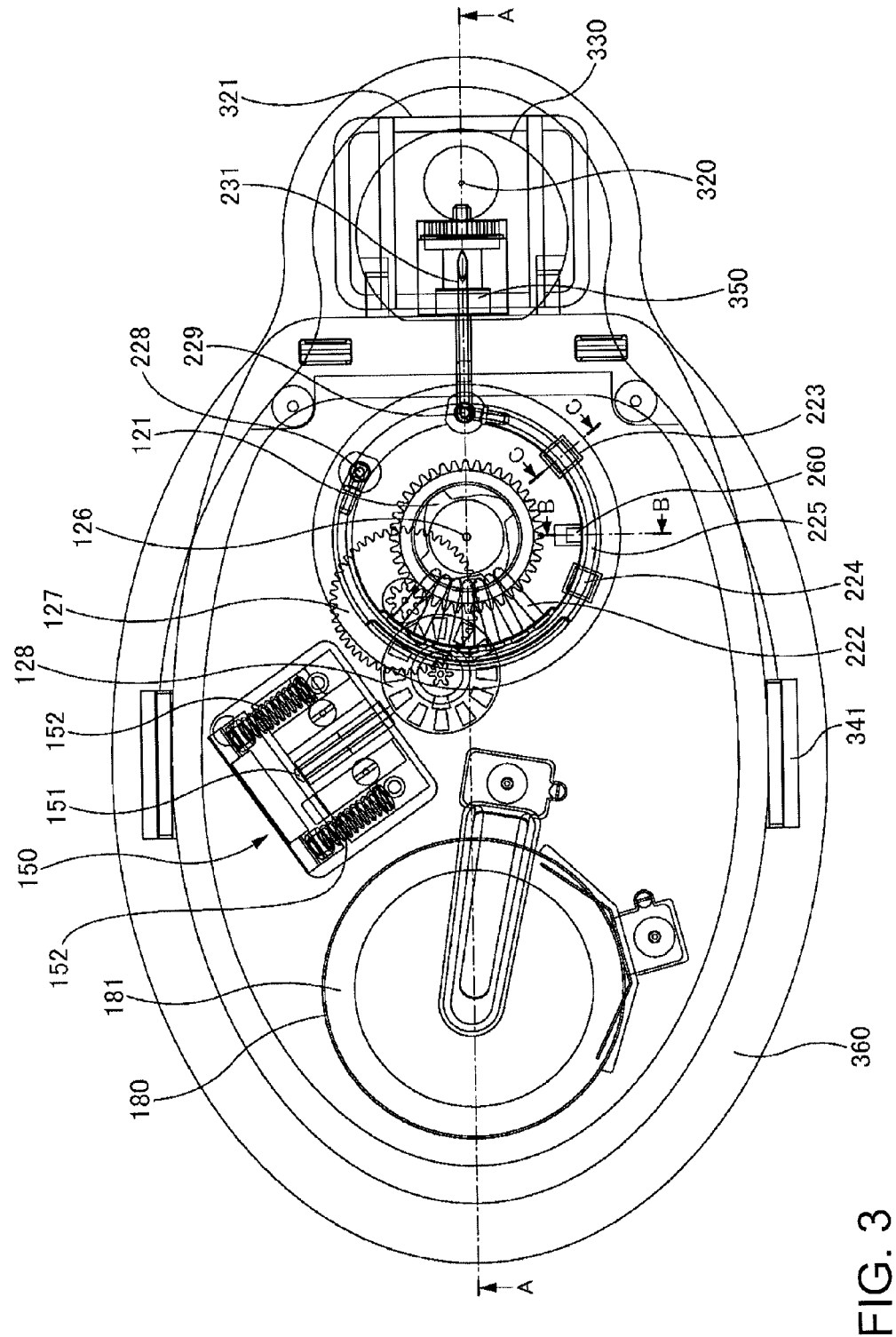
FIG. 3 is a perspective plan view of the micropump.
Figure 4:
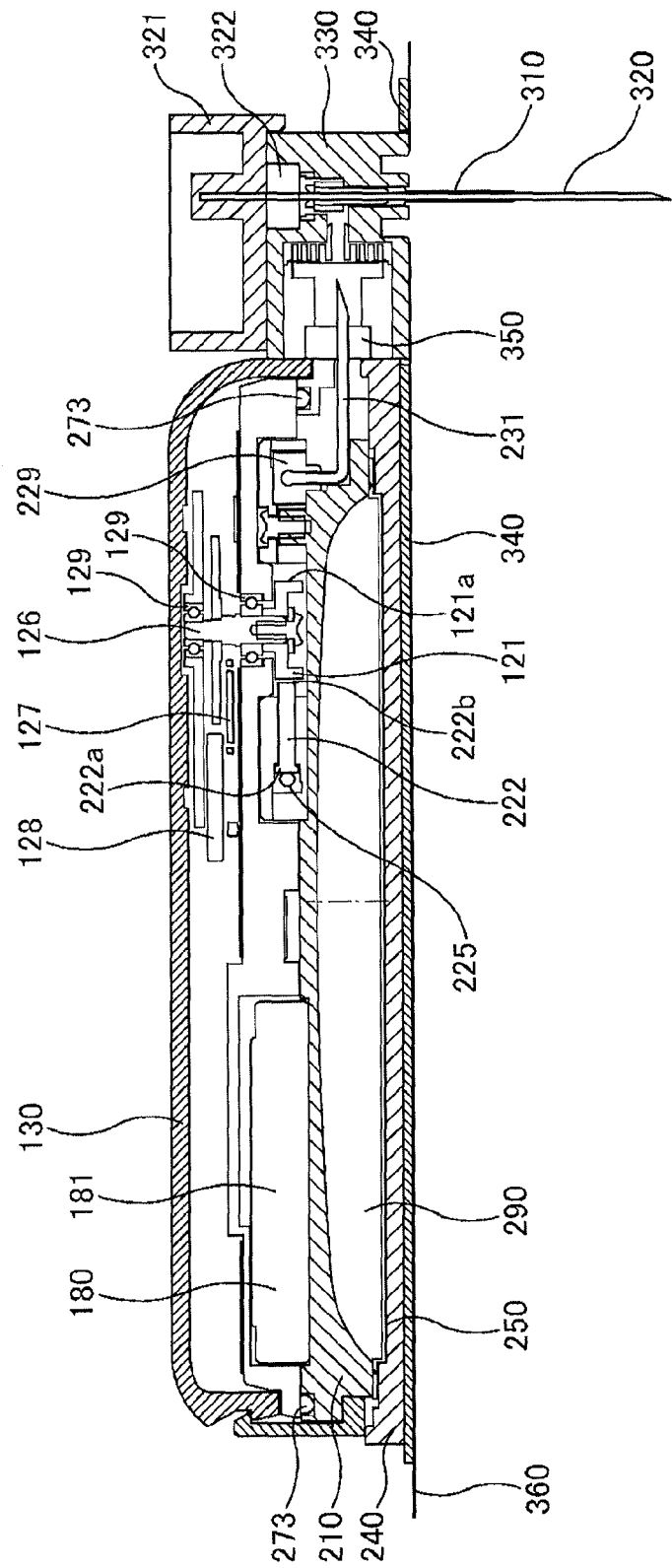
FIG. 4 is a cross-sectional view of the micropump.
Figure 5:
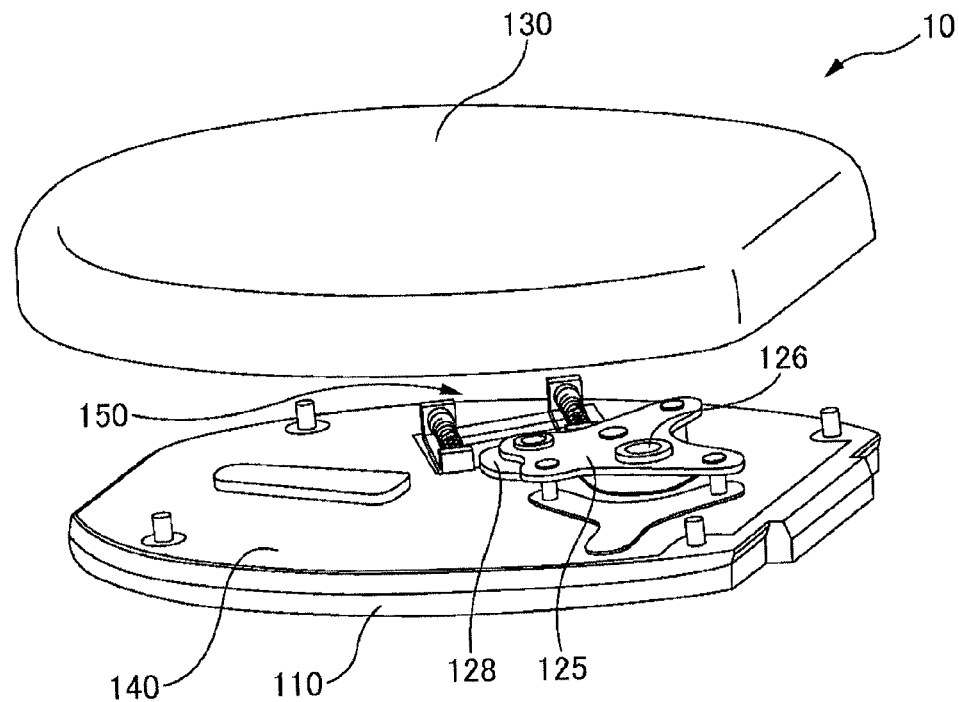
FIG. 5 is a perspective view of the inside of a main body.
Figure 6:
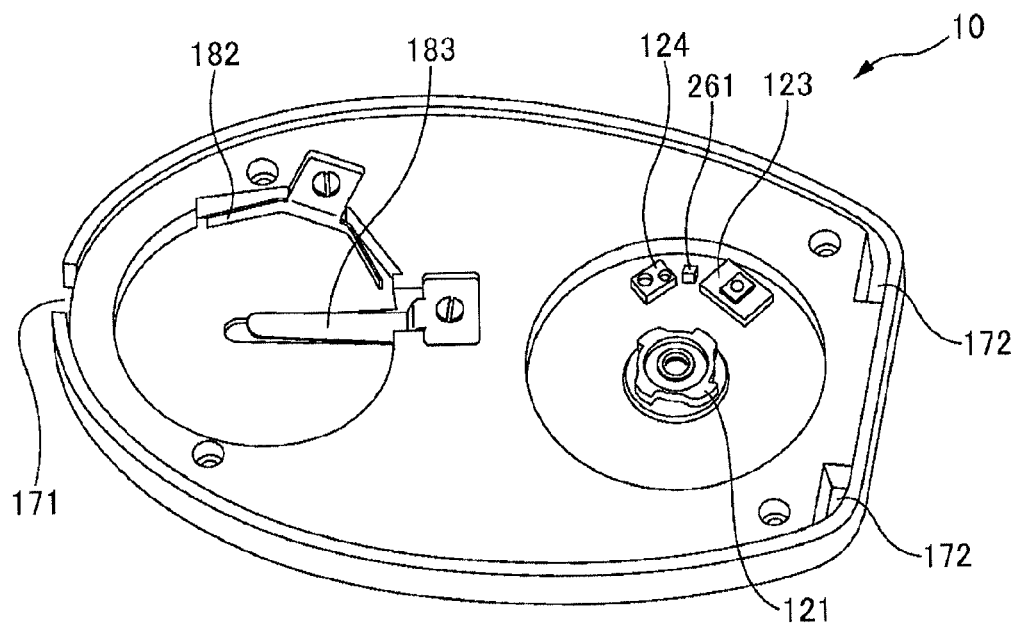
FIG. 6 is a perspective view of the rear surface of the main body.
Figure 7:
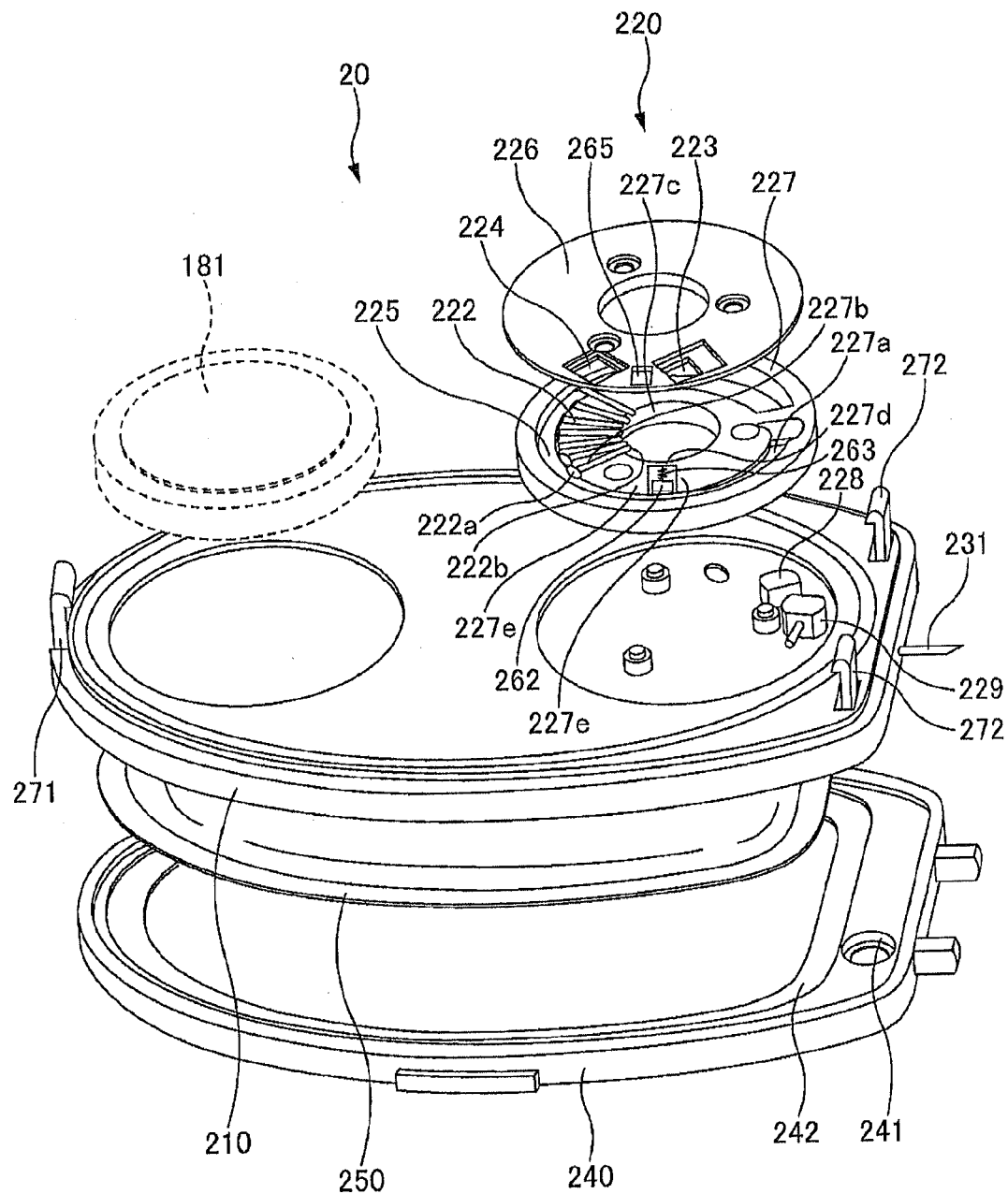
FIG. 7 is an exploded perspective view of a cartridge.
Figure 8:
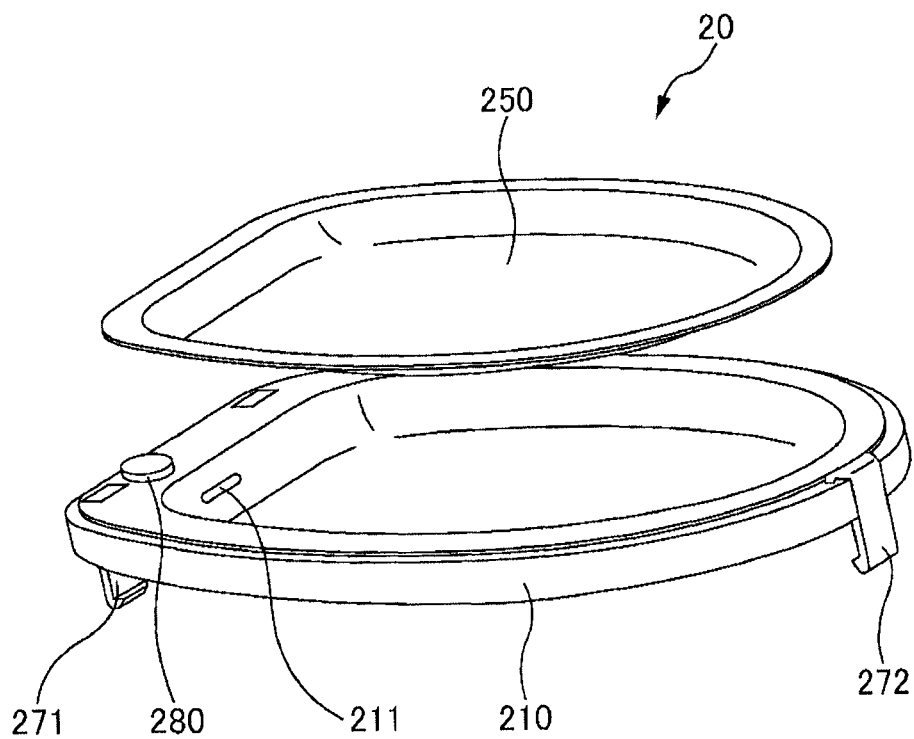
FIG. 8 is a perspective view of the rear surface of a cartridge base.
Figure 9:
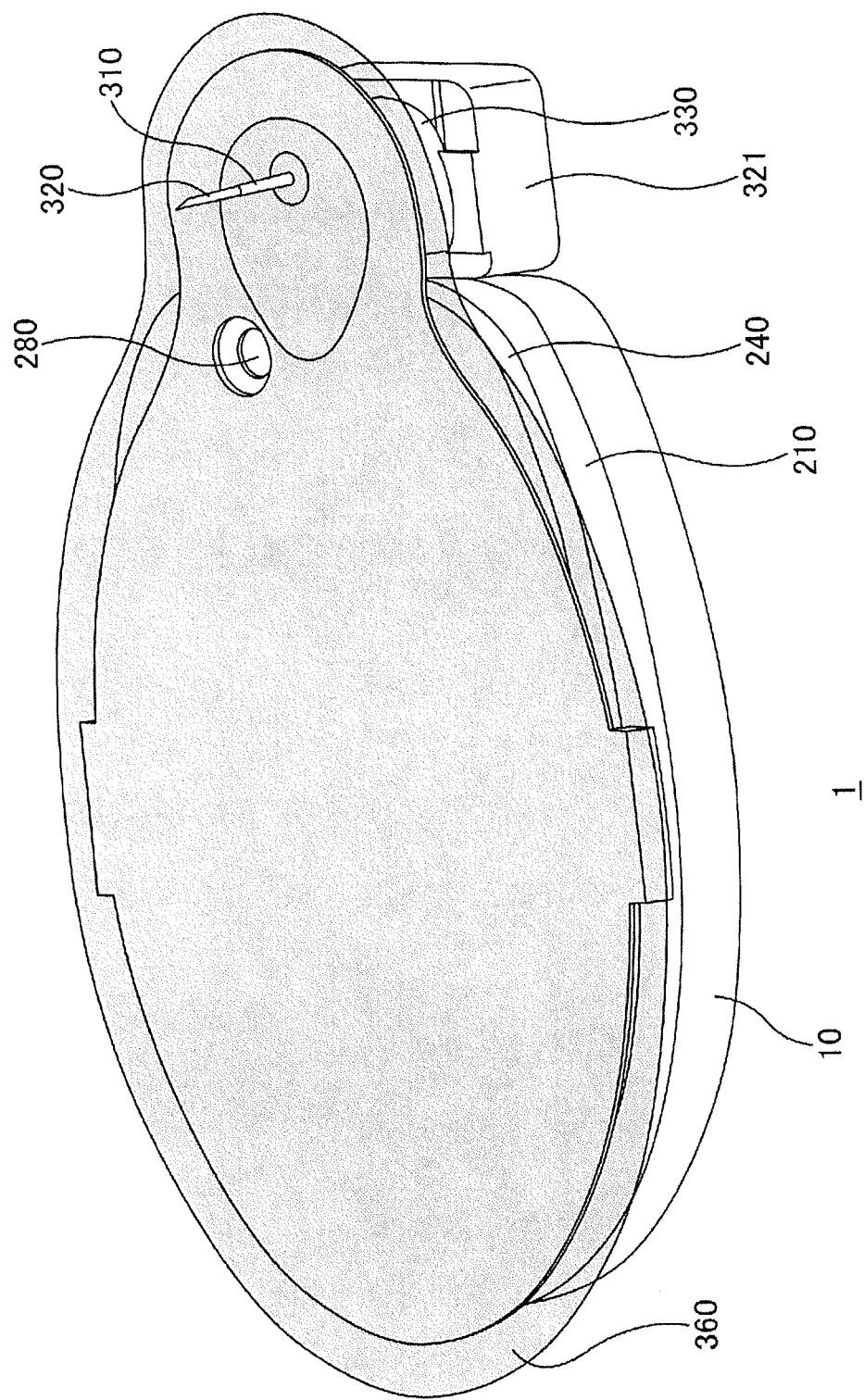
FIG. 9 is a perspective view of the rear surface of the micropump.

FIG. 3 is a perspective plan view of the micropump 1. FIG. 4 is a cross-sectional view of the micropump 1. That is, FIGS. 3 and 4 are diagrams of the main body 10, the cartridge 20, and the injection set 30 which are assembled. FIG. 5 is a perspective view of the inside of the main body 10. FIG. 6 is a perspective view of the rear surface of the main body 10. FIG. 6 is a diagram illustrating the rear surface of FIG. 5 described above. FIG. 7 is an exploded perspective view of the cartridge 20. FIG. 8 is a perspective view of the rear surface of a cartridge base 210. FIG. 9 is a perspective view of the rear surface of the micropump 1.

Hereinafter, each part of the micropump 1 will be described with reference to FIGS. 1 to 9 described above. First, each part in the main body 10 (corresponding to a main body portion) will be described.

The main body 10 includes a main body base 110, each part configured on a main body base 110, and a main body case 130. In addition, each part on the main body base 110 is covered by the main body case 130 to be protected.

The main body 10 includes a circuit board 140 configured on the main body base 110. The circuit board 140 is an electronic board for controlling a piezoelectric motor 150 and the like according to programs. In addition, the main body 10 includes the piezoelectric motor 150. The piezoelectric motor 150 is a motor for applying a rotational driving force to a cam 121, which will be described later.

The piezoelectric motor 150 includes a plate-like member 151 and a pair of springs 152 (FIG. 3). The springs 152 impels the plate-like member 151 toward a rotor wheel 128 using their elastic forces. The plate-like member 151 is impelled toward the rotor wheel 128 as described above such that the tip end portion thereof comes into contact with the circumferential surface of the rotor wheel 128.

The plate-like member 151 is a member configured in layers. The plate-like member 151 includes a piezoelectric layer and two electrodes, and the shape thereof is changed by a change in a voltage applied to the two electrodes. For example, longitudinal vibration and flexural vibration are alternately repeated by the applied voltage. Longitudinal vibration changes the length of the plate-like member 151 in the axial direction thereof, and flexural vibration changes the plate-like member 151 in a substantially S shape. As the vibrations are alternately repeated, the rotor wheel 128 is rotated in a predetermined direction.

The rotor wheel 128 has a pinion that is rotated integrally at a position different in the height direction of the micropump 1, and the pinion is engaged with a gear of an intermediate wheel 127 to rotate the intermediate wheel 127. In addition, the intermediate wheel 127 also has a pinion that is rotated integrally at a position different in the height direction of the micropump 1, and the pinion is engaged with a gear that is rotated integrally with an output shaft 126. The rotor wheel 128, the intermediate wheel 127, and the output shaft 126 are fixed to a gear train support 125 fixed to the main body 10 so that each of the shafts thereof can be rotated.

The cam 121 is also fixed to the output shaft 126 pivotally supported by bearings 129 so as to be integrally rotated. In addition, the cam 121 is also rotated along with the rotation of the output shaft 126. Accordingly, the power from the piezoelectric motor 150 is transmitted to the cam 121.

As illustrated in FIG. 6, a hook holder 171 is provided at the front of the main body 10, and hook insertion openings 172 are provided at two points at the rear thereof. A fixing hook 271 of the cartridge 20 is hooked to the hook holder 171, and fixing hooks 272 are hooked to the hook insertion openings 172 so that the cartridge 20 can be fixed to the main body 10 (FIGS. 2 and 4).

At this time, a packing 273 is fitted to a groove portion of the outer periphery of the upper surface of the cartridge base 210. Therefore, when the main body 10 and the cartridge 20 are fixed to each other, a space formed by the main body 10 and the cartridge 20 can be sealed so as not to allow a liquid or the like to infiltrate into the space.

The main body 10 includes a clogging detection element 123 and a bubble detection element 124 at the rear surface thereof (FIG. 6). The clogging detection element 123 includes, for example, a pressure sensor. In addition, when the main body 10 and the cartridge 20 are assembled in one body, the pressure sensor comes into contact with a portion of a tube 225. When the tube 225 is clogged at the downstream side or a position therebelow, the internal pressure of the tube 225 is increased, and the tube 225 itself expands. Therefore, at this time, the tube 225 presses the pressure sensor. Accordingly, by monitoring the pressure detected by the pressure sensor, whether or not the tube is clogged at the downstream side or position therebelow can be determined.

In addition, the bubble detection element 124 includes, for example, an optical sensor. The optical sensor illuminates the tube 225 with light, and detects the reflected light. In addition, the optical sensor can detect a difference between reflected light when a liquid occupies the inside of the tube 225 and reflected light when bubbles occur. Accordingly, whether or not bubbles occur in the tube 225 can be determined.

In addition, the main body 10 includes a secondary battery storage portion 180 at the rear surface thereof (FIG. 6). The secondary battery storage portion 180 has a battery positive terminal 182 and a battery negative terminal 183, and by inserting a secondary battery 181 into the secondary battery storage portion 180, predetermined power can be supplied to each part of the main body 10.

Next, the cartridge 20 (corresponding to a cartridge portion) will be described.

The cartridge 20 includes the cartridge base 210, a cartridge base presser 240, and each part configured on the cartridge base 210. The cartridge base 210 configures a storage portion 290 together with a reservoir film 250 as described later.

The cartridge base 210 of the cartridge 20 includes a finger unit 220 on the upper surface thereof. The finger unit 220 includes a finger base 227, fingers 222, the tube 225, and a finger presser 226. In addition, on the upper surface of the cartridge base 210, a suction connector 228 and a discharge connector 229 are provided. The suction connector 228 is a connector 228 for suctioning a liquid in the finger unit 220, and the discharge connector 229 is a connector for discharging the liquid from the finger unit 220.

A plurality of grooves are formed in the finger base 227, and the suction connector 228 and the discharge connector 229 are inserted into the grooves. In addition, in the finger base 227, a tube guide groove 227a that guides the tube 225 is formed in an arc shape to accommodate the tube 225. One end of the tube 225 is densely connected to the suction connector 228, and the other end thereof is densely connected to the discharge connector 229.

A plurality of finger guides 227b are formed on the inside of the arc formed by the tube guide groove 227a. The finger guides 227b respectively accommodate the fingers 222. Accordingly, a tip end 222a of the finger 222 is disposed to be in a direction substantially perpendicular to the tube 225.

The finger presser 226 is fixed to the upper surface of the finger base 227 by a fixing screw (not illustrated). Accordingly, the finger 222 is able to slide only in a direction along the finger guide 227b.

As described above, since the fingers 222 and the tube 225 are provided on the cartridge 20 side, even in a case where a tube having a diameter different from that of the tube 225 is employed, the cartridge 20 in which the fingers 222 having a length that matches the diameter of the tube are assembled can be provided. Accordingly, even when the size of the cam 121 is a standardized size, a cam surface 121a of the cam 121 can be appropriately disposed at a position that abuts on a rear end portion 222b of the finger 222.

A clogging detection window 223 and the bubble detection window 224 are provided in the finger presser 226. When the main body 10 and the cartridge 20 are assembled, the clogging detection element 123 detects clogging of the liquid in the tube 225 via the clogging detection window 223. In addition, the bubble detection element 124 detects presence or absence of bubbles in the tube 225 via the bubble detection window 224.

An injection set connection needle 231 is provided at the side surface of the cartridge base 210 to enable the liquid to be sent to the injection set 30 via a patch septum 350. The injection set connection needle 231 communicates with the discharge connector 229. On the other hand, the suction connector 228 communicates with the storage portion 290, which will be described later, via a through-hole provided in the cartridge base 210. Accordingly, the liquid in the storage portion 290 can be supplied to the injection set connection needle 231 through the suction connector 228, the tube 225, and the discharge connector 229.

As illustrated in FIG. 4, in this embodiment, the tip end position of the injection set connection needle 231 has substantially the same height as the storage portion 290 in the height direction. Accordingly, although the liquid passes through the tube 225 and the like on the upper surface of the cartridge 20, the height difference itself between the tip end position of the injection set connection needle 231 and the position of the storage portion 290 is small. Therefore, the potential energy difference can be reduced, and thus the liquid stored in the storage portion 290 can be sent to the injection set connection needle 231 with little energy. This configuration is advantageous in a case where the power saving type piezoelectric motor 150 described above is used.

The cartridge 20 includes the reservoir film 250. The periphery of the reservoir film 250 is pinched between the cartridge base 210 and a film pressing portion 242 provided in the cartridge base presser 240. Accordingly, the storage portion 290 is configured between the reservoir film 250 and the cartridge base 210 such that the liquid can be stored in the storage portion 290.

The cartridge base 210 is made of a plastic and the surface thereof on a side where the reservoir film 250 is provided has a curved surface shape. As such, the storage portion 290 has a curved surface shape, and the film of the reservoir film 250 can be deformed according to the residual amount of the liquid stored in the storage portion 290. Therefore, the fluid can be squeezed out so as not to be left in the storage portion 290. In addition, it is preferable that the reservoir film 250 at this time be processed to have a curved surface shape along the above-mentioned curved surface shape. Accordingly, even when the amount of fluid in the storage portion 290 is reduced, the reservoir film 250 is deformed along the curved surface, and thus the liquid can be squeezed out so as not to be left.

The reservoir film 250 is configured as a multi-layer film. At this time, the inner layer is preferably made of polypropylene, and as the material of the outer layer, a material having excellent gas barrier properties is preferably selected. In addition, the reservoir film 250 is not limited to this, and for example, may be made of a thermoplastic elastomer or may be a film made by pasting another material to the thermoplastic elastomer.

A cartridge septum 280 is provided on the lower surface side of the cartridge 20 (FIG. 9). The cartridge septum 280 is inserted into a cartridge septum insertion hole 241 provided in the cartridge base presser 240 when the cartridge base 210 and the cartridge base presser 240 are assembled. One surface of the cartridge septum 280 is exposed to opening portions 340a and 360a of a patch base 340 and an adhesive tape 360 (FIGS. 2 and 9), and the other surface thereof communicates with a fluid inlet port 211. The fluid inlet port 211 is open between the reservoir film 250 and the cartridge base 210. Therefore, the liquid to be injected using an injection needle or the like via the cartridge septum 280 is stored in the storage portion 290.

Next, the injection set 30 (corresponding to an injection portion) will be described with reference to mainly FIG. 4.

The injection set 30 includes a catheter 310, an introduction needle 320, an introduction needle folder 321, an introduction needle septum 322, a port base 330, the patch base 340, the patch septum 350, and the adhesive tape 360.

The injection set connection needle 231 is inserted through the patch septum 350 as described later to supply the liquid to the injection set 30. The patch septum 350 is provided in the side wall portion of the injection set 30, and accordingly, the injection set connection needle 231 penetrates through the patch septum 350 when the reservoir 20 is mounted toward the side surface of the injection set 30.

In addition, the septum of the patch septum 350 is formed of a material (for example, silicone) so that a hole that is open due to the penetration of a needle or the like is blocked. Accordingly, even when the needle is inserted through and removed from the septum, the liquid or the like does not leak out via the septum.

The catheter 310 is a tube for injecting the liquid. A portion of the catheter 310 is held by the port base 330, and a portion thereof is exposed on the lower side of the port base 330. In order to inject the liquid by using the injection set 30, the exposed portion of the catheter 310 is placed into a living body or the like and the liquid is continuously injected. Therefore, the catheter 310 is formed of a soft material such as a fluororesin.

The introduction needle 320 is a hollow long and thin needle-like member, and the external shape thereof is smaller than the inside diameter of the catheter 310. The introduction needle 320 is inserted into the catheter 310 before use. The sharp end side of the introduction needle 320 is exposed in the downward direction of the catheter 310, and the other end side thereof is fixed to the introduction needle folder 321. In addition, before use, the introduction needle 320 is inserted through the introduction needle septum 322 fixed into the port base 330.

In this configuration, the introduction needle 320 is drawn from the inside of the catheter 310 by drawing the introduction needle folder 321 from the port base 330. However, the liquid that flows from the injection set connection needle 231 does not leak out from the introduction needle septum 322 side and flows into the living body through the catheter 310.

The injection set 30 includes the patch base 340. The patch base 340 is fixed to the port base 330, includes a cartridge fixing member 341, and has a function of fixing the cartridge 20 to the injection set 30. In order to connect the cartridge 20 to the injection set 30, the cartridge 20 is moved to slide from the left of FIG. 2 toward the injection set 30. In addition, the injection set connection needle 231 provided in the cartridge 20 penetrates through the patch septum 350 and is inserted into the injection set 30.

The patch base 340 includes the adhesive tape 360 at the lower surface thereof. In addition, the micropump 1 is able to stick to the living body or the like.

In the above configuration, when the main body 10 and the cartridge 20 are assembled in one body, the clogging detection element 123 is disposed above the clogging detection window 223, and the bubble detection element 124 is disposed above the bubble detection window 224. Accordingly, by monitoring the tube 225, occurrence of clogging of the liquid and occurrence of bubbles in the tube 225 can be detected.

In addition, when the main body 10 and the cartridge 20 are assembled, the cam 121 of the main body 10 is inserted into a cam accommodation portion 227c of the finger base 227. Accordingly, the cam surface 121a of the cam 121 is disposed at a position that opposes the rear end portion 222b of the finger 222. In addition, as the cam 121 is rotated, the cam surface 121a abuts on the rear end portion 222b of the finger 222 to enable the finger 222 to slide.

Figure 10:
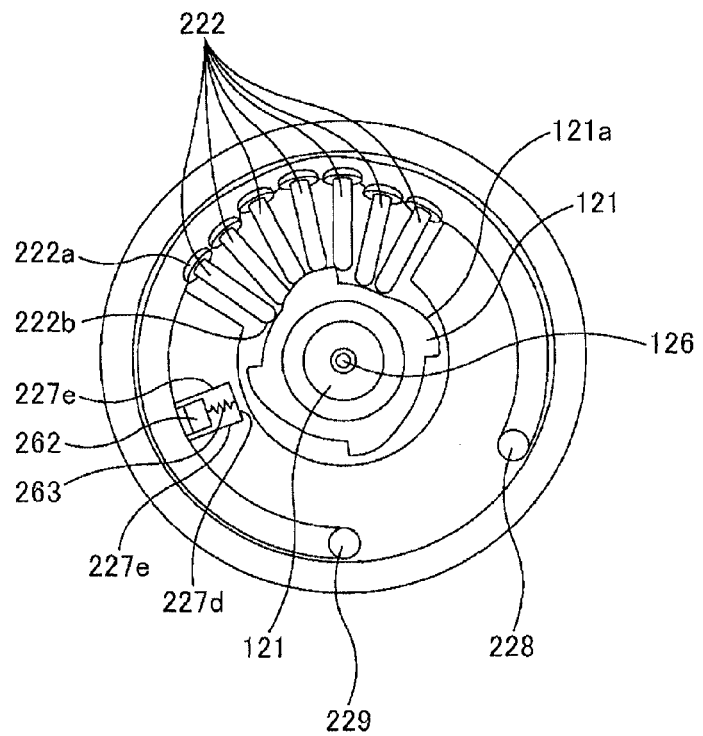
FIG. 10 is a diagram illustrating a rotary finger pump.

FIG. 10 is a diagram illustrating a rotary finger pump. The cam 121 is provided with four cam noses. Each of the cam noses has a shape in which the height thereof is transited to be gradually increased from the lowest portion of the cam nose to the highest portion, and when the height reaches the highest portion, the height is transited to the lowest portion of the adjacent cam nose. By employing this shape, when the cam 121 is rotated, the tip end portions 222a of the plurality of fingers 222 sequentially press the tube 225 in a direction from the suction connector 228 side to the discharge connector 229 side. In addition, the liquid in the tube 225 can be sent to the discharge connector 229 side from the suction connector 228 side.

In this configuration, the tube 225, the finger unit 220, the cam 121, and the piezoelectric motor 150, which correspond to a pump portion, are disposed closer to the outer side than the storage portion 290 with respect to the living body, and thus the storage portion 290 that stores the liquid can be protected by the pump portion. In addition, the storage portion 290 is less likely to be broken.

Further, a reduction in the size of the micropump 1 provided with the storage portion 290 and the pump portion is preferable. Through the laminated arrangement described above, a further reduction in the size can be realized. At this time, since the storage portion 290 is provided on the living body side, the temperature of the liquid in the storage portion 290 can be kept by the body temperature of the living body.

In addition, in FIGS. 7 and 10, a tube blocking pin 262 and a tube blocking spring 263 which are parts of an automatic blocking portion 260, which will be described later, are illustrated. In addition, aside wall 227e (corresponding to a guide member) which guides the movement of the tube blocking pin 262 in a direction toward the tube 225 and a rear end wall 227d to which one end of the tube blocking spring 263 is fixed are illustrated. Hereinafter, the automatic blocking portion 260 will be described.

Automatic Blocking Portion 260

Figure 11:
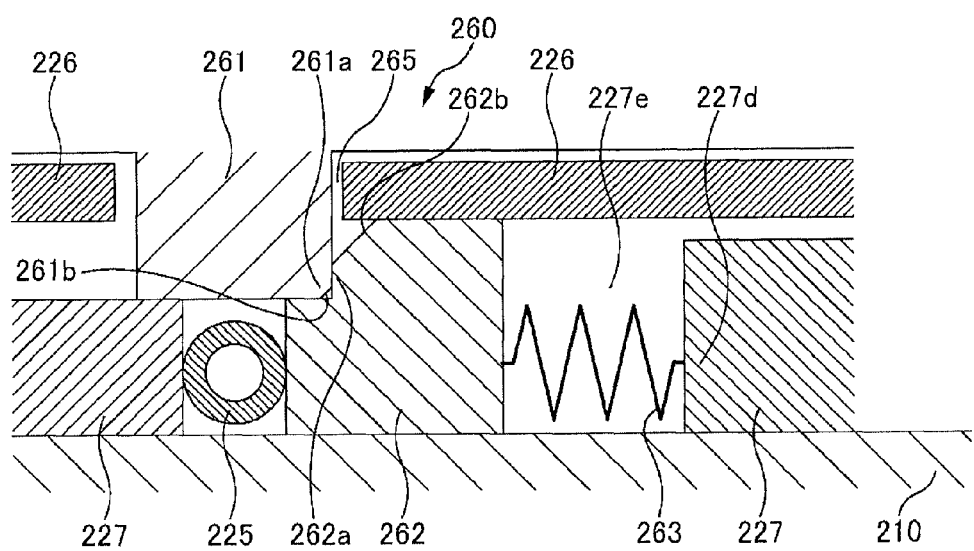
FIG. 11 is a cross-sectional view taken along the line B-B in FIG. 3 before blocking.
Figure 12:
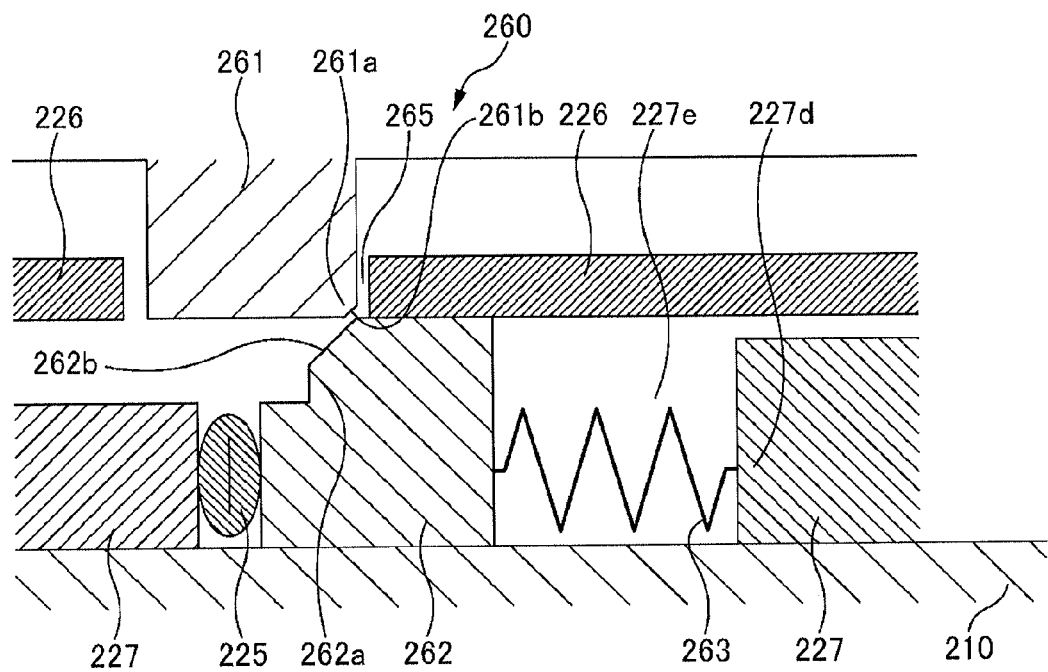
FIG. 12 is a cross-sectional view taken along the line B-B in FIG. 3 after blocking.

FIG. 11 is a cross-sectional view taken along the line B-B in FIG. 3 before blocking. FIG. 12 is a cross-sectional view taken along the line B-B in FIG. 3 after blocking. Hereinafter, the configuration and the operation of the automatic blocking portion 260 will be described with reference to the drawings in addition to the above-described drawings.

The automatic blocking portion 260 includes a main body side tube opening protrusion 261 (corresponding to an engagement member), the tube blocking pin 262 (corresponding to a blocking member), and the tube blocking spring 263 (corresponding to an impelling member). Among these, the main body side tube opening protrusion 261 is provided between the clogging detection element 123 and the bubble detection element 124 of the main body 10 so as to be fixed (FIG. 6). On the other hand, the tube blocking pin 262 and the tube blocking spring 263 are provided on the cartridge 20 side.

The tube blocking pin 262 and the tube blocking spring 263 are accommodated in the finger base 227. One end of the tube blocking spring 263 is fixed to the rear end side of the tube blocking pin 262. In addition, the other end of the tube blocking spring 263 is fixed to the rear end wall 227d provided in the finger base 227.

Accordingly, the tube blocking pin 262 is impelled in a direction toward the tube 225. However, when the cartridge 20 is mounted to the main body 10, the movement of the tube blocking pin 262 is restricted by the main body side tube opening protrusion 261 that is inserted through an insertion window 265 of the finger presser 226 and the tube 225 is not blocked. This is because an engagement portion 261a of the main body side tube opening protrusion 261 is caught on an engagement portion 262a provided in the tube blocking pin 262.

On the other hand, when the cartridge 20 is not mounted to the main body 10, the inserted main body side tube opening protrusion 261 is pulled out of the insertion window 265, and the above-described engagement is released. Accordingly, the tube blocking pin 262 which is impelled in the direction toward the tube 225 by the tube blocking spring 263 blocks the tube 225 together with the wall surface of the finger base 227.

In order to mount the cartridge 20 to the main body 10 again, the main body side tube opening protrusion 261 is inserted into the insertion window 265, and a sliding tilted surface 261b provided in the main body side tube opening protrusion 261 and the sliding tilted surface 262b provided in the tube blocking pin 262 slide on each other such that the tube blocking pin 262 is moved in such a direction that the tube blocking spring 263 is compressed. In addition, the engagement portion 261a of the main body side tube opening protrusion 261 is caught on the engagement portion 262a provided in the tube blocking pin 262 again.

According to the above-described micropump 1, when the cartridge 20 is mounted to the main body 10, the cam 121 presses at least one finger 222 and thus the tube 225 is blocked at the position of the pressed finger 222. In addition, the blocking of the tube 225 by the automatic blocking portion 260 is released. On the other hand, when the cartridge 20 is detached from the main body 10, the tube 225 is blocked by the automatic blocking portion 260.

In the micropump 1, when the cartridge 20 is detached from the main body 10, the cam 121 that restricts the movement of the fingers 222 is also detached and thus the blocking of the tube 225 by the finger 222 is released. However, in the above-described configuration, the tube 225 can be blocked by the automatic blocking portion 260 and thus the liquid can be prevented from freely flowing.

In addition, the automatic blocking portion 260 is provided on the downstream side of the fingers 222 in the flowing direction of the liquid of the tube 225. Accordingly, there is a possibility that the tube 225 may be pressed by the finger 222 which freely moves when the cartridge 20 is detached from the main body 10. However, since the tube 225 is blocked by the automatic blocking portion 260 that is provided on the downstream side thereof, the liquid can be prevented from freely flowing toward the downstream side.

Clogging Detection Portion

Figure 13:
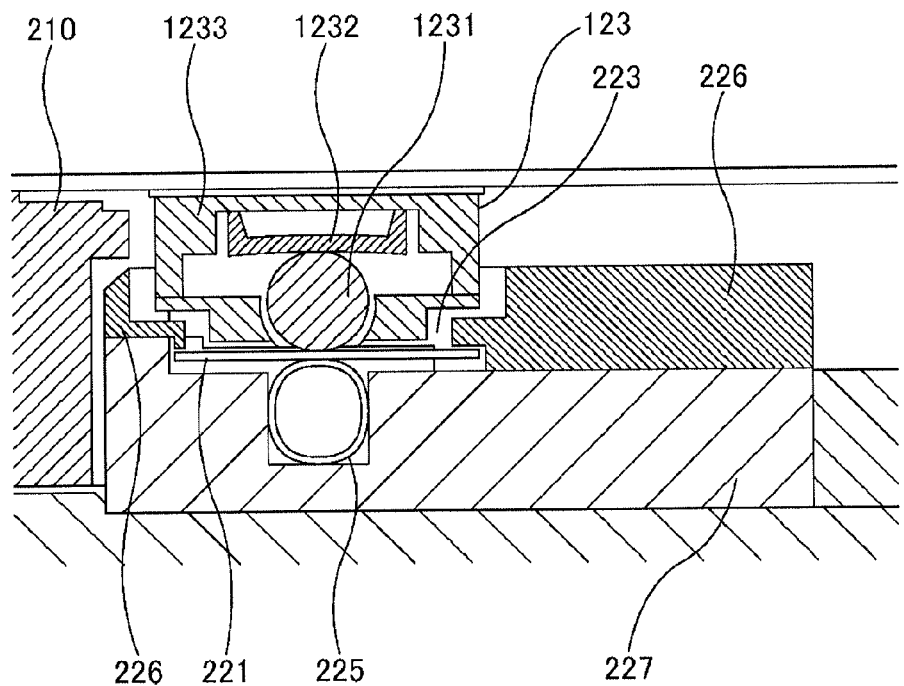
FIG. 13 is a cross-sectional view taken along the line C-C in FIG. 3 during mounting.
Figure 14:
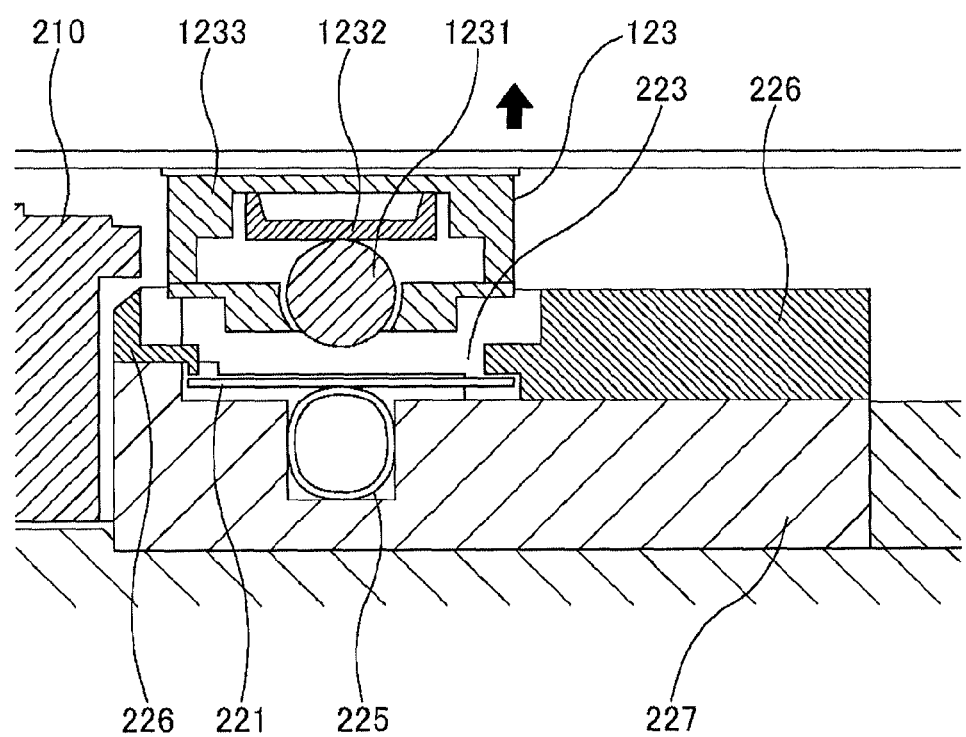
FIG. 14 is a cross-sectional view taken along the line C-C in FIG. 3 during separation.

FIG. 13 is a cross-sectional view taken along the line C-C in FIG. 3 during mounting. FIG. 14 is a cross-sectional view taken along the line C-C in FIG. 3 during separation. Hereinafter, a clogging detection portion will be described with reference to the drawings. The clogging detection portion also functions as a detecting device that detects the detachment of the cartridge 20 from the main body 10.

The clogging detection portion includes the clogging detection element 123, a pressure transmission plate 221, and a clogging detection window 223 formed in the finger presser 226.

The clogging detection element 123 is the pressure sensor. The clogging detection element 123 includes a semiconductor force sensor element 1232, a spherical body 1231, and an accommodation member 1233 that accommodates them. The semiconductor force sensor element 1232 is formed by using a Si semiconductor substrate that detects a force. The semiconductor force sensor element 1232 converts an applied force into an electric signal by using a piezoresistive effect and outputs the electric signal. In addition, the output electric signal is sent to the circuit board 140. The spherical body 1231 is used for transmitting a force which is an object of measurement to the semiconductor force sensor element 1232.

The clogging detection element 123 is fixed to the main body 10 side as described above. In addition, when the cartridge 20 is attached to the main body 10, one point of the spherical body 1231 comes in contact with the pressure transmission plate 221. The area of the pressure transmission plate 221 is greater than the opening area of the clogging detection window 223 for use. In addition, the end portion of the pressure transmission plate 221 is interposed between the finger presser 226 and the finger base 227 to be slightly movable in the vertical direction. The pressure transmission plate 221 comes in contact with the tube 225 on the opposite surface to the surface that comes in contact with the spherical body 1231. When the cartridge 20 is attached to the main body 10, the tube 225 and the pressure transmission plate 221 abut on each other, and the pressure transmission plate 221 and the spherical body 1231 abut on each other.

In a case where the flow path of the liquid is clogged and a flow occurs in the tube 225 due to the finger unit 220, the internal pressure of the tube 225 is increased, and thus the tube 225 which is an elastic body expands. When the tube 225 expands, the side surface of the tube 225 presses the spherical body 1231 of the clogging detection element 123 via the pressure transmission plate 221 in the clogging detection window 223. Therefore, by monitoring the pressure detected by the clogging detection element 123 using the circuit board 140, clogging of the tube 225 can be detected when the pressure becomes higher than a predetermined pressure.

In this embodiment, particularly, since the pressure transmission plate 221 is provided in the clogging detection window 223, a pressing force of the tube 225 that expands in the clogging detection window 223 is reliably transmitted to the spherical body 1231 via the pressure transmission plate 221. At this time, a force obtained by multiplying the pressure of the tube 225 by the area of the pressure transmission plate 221 is transmitted to the spherical body 1231. Therefore, clogging of the fluid can be detected with high sensitivity.

In this embodiment, as the pressure sensor, the clogging detection element 123 having the spherical body 1231 is used. The spherical body 1231 comes in contact with the pressure transmission plate 221 at one point in theory. Therefore, the clogging detection element 123 can detect the movement of the pressure transmission plate 221 with good sensitivity.

In addition, since the clogging detection portion as described above is provided, even in a case where a member that is narrower than the inside diameter of the tube 225 and is likely to be clogged like the injection set connection needle 231 is included on the downstream side of the clogging detection element 123 in the tube 225, clogging of the tube 225 can be detected with good sensitivity.

In addition, as illustrated in FIG. 13, when the main body 10 and the cartridge 20 are assembled, the assembly may be performed so that the tube 225 applies a predetermined pressure to the clogging detection element 123 in advance. Accordingly, the clogging detection element 123 always outputs an electric signal indicating that the predetermined pressure is applied. On the other hand, as illustrated in FIG. 14, when the cartridge 20 is separated from the main body 10, the tube 225 cannot press the clogging detection element 123 at all, and thus the pressure detected by the clogging detection element 123 becomes zero. Therefore, by monitoring the output of the clogging detection element 123, separation of the cartridge 20 from the main body 10 can be detected.

Other Embodiments

The micropump 1 described above achieves a reduction in size and a reduction in thickness and thus allows a small amount of fluid to stably and continuously flow. Therefore, the micropump 1 is mounted into a living body or on the surface of a living body and is appropriate for medical uses such as the development of new drugs or drug delivery. In addition, in various mechanical devices, the micropump 1 may be mounted inside the device or outside the device to be used for transport of fluid such as water or a saline solution, liquid medicine, oils, aromatic liquid, ink, or gas. Moreover, the micropump as a single member can be used for flowing or supplying a fluid.

In addition, in the above-described embodiment, the tube 225 is blocked by impelling the tube blocking pin 262 by the impelling force of the tube blocking spring 263. However, the blocking method is not limited thereto. For example, the tube 225 may also be blocked by a member on a lever, or the tube 225 may also be blocked by a configuration using a link mechanism or the like.

In addition, in the above-described embodiment, the area of the pressure transmission plate 221 is greater than the clogging detection window 223 but may also be substantially the same as the size of the clogging detection window 223.

In addition, a member that transmits a force to the semiconductor force sensor element 1232 is the spherical body 1231 but is not limited to the spherical body. A polyhedron shape such as a rectangular parallelepiped or a cube shape may also be employed.

In addition, in the above-described embodiment, the semiconductor force sensor element 1232 is used as the pressure sensor. However, the pressure sensor is not limited thereto, and any type of pressure sensor may be employed.

The above-described embodiments are for facilitating the understanding of the invention and should not be construed to limit the invention. The invention can be modified and improved without departing from the spirit and naturally includes the equivalents thereof.

The entire disclosure of Japanese Patent Application No. 2012-232578, filed Oct. 22, 2012 is expressly incorporated by reference herein.

What is claimed is:

1. A fluid injecting apparatus comprising:
    a cartridge portion which has a tube that transports a fluid and a blocking member that blocks the tube; and
    a main body portion which is attachable to and detachable from the cartridge portion,
    wherein the blocking member presses the tube to block the tube when the cartridge portion is detached from the main body portion and the blocking of the tube by the blocking member is automatically released when the cartridge portion is mounted to the main body portion.

2. The fluid injecting apparatus according to claim 1,
    wherein the cartridge portion has a plurality of fingers which abut on the tube,
    the main body portion has a cam that displaces the plurality of fingers, and
    when the cartridge portion is mounted to the main body portion, the tube is blocked as the cam abuts on at least one of the fingers.

3. The fluid injecting apparatus according to claim 2,
    wherein the main body portion includes an engagement member,
    the cartridge portion includes an impelling member that impels the blocking member toward the tube, and
    when the cartridge portion is mounted to the main body portion, the engagement member is engaged so that the blocking member is in a state of not blocking the tube.

4. The fluid injecting apparatus according to claim 3,
    wherein, when the cartridge portion is detached from the main body portion, the engagement is released, and the blocking member blocks the tube by the impelling force of the impelling member.

5. The fluid injecting apparatus according to claim 1, further comprising:
    a guide member which guides a movement of the blocking member in a direction toward the tube.

6. The fluid injecting apparatus according to claim 1,
    wherein the tube is made of an elastic material that is deformable.

7. The fluid injecting apparatus according to claim 1,
    wherein the blocking member is provided on a downstream side of the fingers in a transport direction of the fluid.

8. The fluid injecting apparatus according to claim 1, further comprising:
    a needle member provided on a downstream side of the blocking member in the transport direction of the fluid; and
    a storage portion which stores the fluid on an upstream side of the fingers.

9. The fluid injecting apparatus according to claim 1,
    wherein the main body portion includes a pressure sensor that detects a pressure of the tube, and
    the detachment of the cartridge portion from the main body portion is detected on the basis of the detection of the pressure sensor.

10. The fluid injecting apparatus according to claim 1,
    wherein the cartridge portion includes an impelling member that impels the blocking member toward the tube; and
    the blocking member is moved toward the tube by the impelling member and presses the tube to block the tube when the cartridge portion is detached from the main body portion, and the blocking of the tube by the blocking member is automatically released when the cartridge portion is mounted to the main body portion.

11. The fluid injecting apparatus according to claim 1,
    wherein the main body portion has a protrusion, and
    the blocking member is disposed in a blocking position such that the blocking member presses the tube to block the tube when the cartridge portion is detached from the main body portion, and the protrusion moves the blocking member to a block releasing position such that the blocking of the tube by the blocking member is automatically released when the cartridge portion is mounted to the main body portion.

* * * * *